United States Patent [19]

Ponticello et al.

[11] Patent Number: 5,212,253
[45] Date of Patent: May 18, 1993

[54] ELECTROPHORESIS ELEMENT COMPRISING A POLYMER CONTAINING A HALOACETAMIDO GROUP

[75] Inventors: Ignazio S. Ponticello, Pittsford; David B. LaTart, Rochester, both of N.Y.

[73] Assignee: Eastman Kodak Company, Rochester, N.Y.

[21] Appl. No.: 430,995

[22] Filed: Nov. 2, 1989

Related U.S. Application Data

[63] Continuation-in-part of Ser. No. 339,456, Apr. 18, 1989, abandoned.

[51] Int. Cl.$^5$ .............................. C08F 8/00; C08F 8/34
[52] U.S. Cl. .............................. 525/328.2; 525/328.4; 525/350; 525/381; 525/384
[58] Field of Search .................. 525/328.2, 328.4, 350, 525/326.3, 381, 382, 384, 331.4, 330.7

[56] References Cited

U.S. PATENT DOCUMENTS

| | | | |
|---|---|---|---|
| 2,789,958 | 4/1957 | Fettes | 528/109 |
| 3,291,776 | 12/1966 | Newey | 528/109 |
| 3,625,694 | 12/1971 | Cohen et al. | |
| 4,161,407 | 7/1979 | Campbell | |
| 4,193,795 | 3/1980 | Campbell et al. | 430/213 |
| 4,201,840 | 5/1980 | Campbell et al. | 430/17 |
| 4,548,870 | 10/1985 | Ogawa et al. | 428/474.4 |
| 4,582,868 | 4/1986 | Ogawa et al. | 524/211 |
| 4,704,198 | 11/1987 | Ebersole et al. | 204/182.8 |

*Primary Examiner*—Christopher Henderson

[57] ABSTRACT

Described are novel acrylic monomers, homopolymers and copolymers prepared therefrom, and electrophoresis gel media prepared by crosslinking certain copolymers of the invention by a crosslinking reaction that does not involve a free-radical vinyl addition mechanism.

4 Claims, No Drawings

ELECTROPHORESIS ELEMENT COMPRISING A POLYMER CONTAINING A HALOACETAMIDO GROUP

CROSS-REFERENCE TO RELATED APPLICATION

This application is a continuation-in-part of copending U.S. application Ser. No. 339,456 filed Apr. 18, 1989 now abandoned. It is also related to the subject matter of application Ser. Nos. 188,821, filed May 2, 1989, issued into U.S. Pat. No. 4,948,480, Aug. 14, 1990; Ser. No. 339,350, filed Apr. 18, 1989 abandoned, continuation-in-part, Ser. No. 430,996; Ser. No. 339,468, filed Apr. 18, 1989 abandoned, continuation-in-part, Ser. No. 431,048; Ser. No. 339,469, filed Apr. 18, 1989 abandoned, continuation-in-part, Ser. No. 431,043.

FIELD OF THE INVENTION

This invention relates to novel acrylic monomers, to polymers, particularly acrylamide based copolymers, prepared from the monomers and to improved polymeric gel media suitable for electrophoretic separation of biopolymers such as proteins and polynucleic acids (DNA, RNA and their derivatives or fragments) prepared from the foregoing acrylamide based copolymers.

DESCRIPTION RELATIVE TO THE PRIOR ART

Acrylamide based copolymers having vinylsulfonyl or chloroethylsulfonyl groups as media for electrophoresis are described in a number of patent publications, for example, U.S. Pat. No. 4,582,868. Such materials are also known to be gelatin hardeners and crosslinkable polymers useful as binders in film formation or for other uses.

U.S. Pat. No. 3,625,694 describes polymer mordants having active aldehyde, chloroalkanoyl (such as chloroacetyl and chloropropionyl), chloroalkyl (such as chloromethyl), vinylsulfonyl, and other active groups for anchoring (crosslinking) the mordant to a gelatin matrix. U.S. Pat. Nos. 4,193,795 and 4,201,840 describe polymer mordants having vinylsulfonyl and chloroethylsulfonyl groups to covalently bind dyes.

U.S. Pat. No. 4,704,198, which issued on Nov. 3, 1987, contains a comprehensive description of various aspects of electrophoresis. As described therein, and in numerous other publications, electrophoresis is based on the principle that charged molecules or substances will migrate when placed in an electric field. Since proteins and other biopolymers (e.g., DNA, RNA, enzymes and some carbohydrates) are charged, they migrate at pH values different from their isoelectric points. The rate of migration depends, among other things, upon the charge density of the protein or biopolymer and the restrictive properties of the electrophoretic matrix or medium. The higher the ratio of charge to mass, the faster an ion will migrate. The more restrictive the medium, the more slowly an ion will migrate. Electrophoresis has the further advantage of generally requiring only very small (i.e., microgram or less) quantities of material for analysis.

Electrophoresis is generally performed in an aqueous solution or gel across which a voltage is applied. It is the voltage gradient that causes the migration of the species being separated. Gradients typically range from 10 volts/cm to many times higher, the magnitude depending on the nature of the separation being formed.

In theory, separation of different proteins could be achieved readily in free solution provided that the molecules differed sufficiently in their charge densities. However, in practice, separations in free solution are difficult to achieve because convective disturbances produced by or occurring during electrophoresis cause distortions of the protein bands. Resolution of the individual proteins is compromised because the bands are broadened. Also, band broadening continues even after the electrophoresis has been stopped because of diffusion of dissolved solute. Therefore, electrophoresis in free solution is rarely performed. In practice, various supporting media are used to minimize convection and diffusion, and to effect separation both on the basis of molecular size and of net charge.

Many support media for electrophoresis are in current use. The most popular are sheets of paper or cellulose acetate, agarose, starch, and polyacrylamide. Paper, cellulose acetate, and similar porous materials are relatively inert and serve mainly for support and to minimize convection. Separation of proteins using these materials is based largely upon the charge density of the proteins at the pH selected.

On the other hand, starch, agarose and polyacrylamide gels not only minimize convection and diffusion but also actively participate in the separation process. These materials provide a restrictive medium in which the average size of the polymeric network opening (or average pore size) can be controlled to achieve a molecular fractionation in a desired molecular size range. In this way, molecular sieving occurs and provides separation on the basis of both charge density and molecular size.

The extent of molecular sieving is thought to depend on how much the gel network opening size (i.e., average pore size) is larger than the size of the migrating particles. The average pore size of agarose gels is so large that molecular sieving of most protein molecules is minimal and separation of proteins in that medium is based mainly on charge density. In contrast, polyacrylamide gels can have openings whose sizes more closely approximate the sizes of protein molecules and so contribute to the molecular sieving effect. Polyacrylamide has the further advantage of being a synthetic polymer which can be prepared in highly purified form.

With agarose, a polysaccharide, the gel is formed by casting a heated (T>50° C.) agarose solution and allowing the solution to cool. This process of gelation on cooling is similar overall, and even on a molecular basis, to the formation of gelatin gels from cooled solutions of gelatin in water. Agarose is rarely used at concentrations higher than 5% because such solutions are very viscous and not easily poured. Agarose is therefore widely used at concentrations <5% (w/v) for the electrophoresis of large molecules, e.g., high molecular weight proteins, and polynucleotides.

The ability to produce gels having a wide range of polymer concentrations (and, therefore, since the gel network opening decreases with increasing polymer concentration, a wide range of controlled average pore sizes) as well as to form pore size gradients within the gels by virtue of polymer concentration gradients, are additional advantages of polyacrylamide as an electrophoresis gel medium. Control over pore size enables mixtures to be sieved on the basis of molecular size and enables molecular weight determinations to be performed. These determinations are especially accurate if the proteins are treated with a detergent, such as sodium dodecyl sulfate (SDS), which neutralizes the effects of inherent molecular charge so that all SDS treated molecules, regardless of size, have approximately the same charge density values. This technique is referred to as SDS-PAGE (Sodium Dodecyl Sulfate-PolyAcrylamide Gel Electrophoresis).

The popularity of polyacrylamide-based electrophoresis gels stems not only from the comparatively wide latitude in polymer content and buffer composition attainable with them, but also from the high degree of inertness in the gel with respect to both the voltages applied and the solutes being separated, the ease with which proteins are detected once separated and good reproducibility with carefully prepared gels.

Conventionally, polyacrylamide gel media for use in SDS-PAGE electrophoresis have been prepared in situ by free radical induced polymerization of a monomer such as acrylamide and a crosslinking agent, most commonly N,N'-methylenebisacrylamide, under oxygen-free conditions in the presence of water, a buffer, a polymerization initiator, and a polymerization catalyst. More particularly, since such polymerization can be inhibited by the presence of oxygen, polyacrylamide gel media for electrophoresis typically are prepared by a process involving: introducing a previously deoxygenated aqueous solution containing acrylamide, a crosslinking (bis) monomer, a buffer, a free radical polymerization initiator and a polymerization catalyst into a cell formed between two glass plates with a selected clearance (e.g., 0.15-3 mm); and sealing the gel-forming solution from oxygen; whereupon the free radical polymerization proceeds so as to prepare the desired gel. Often this is done in situ by the scientist who is to conduct the electrophoresis.

The usual practice is to perform a free radical polymerization with acrylamide and a suitable bis monomer such as N,N'-methylenebisacrylamide (often simply referred to as "bis") in order to obtain a gel. Such gel formation is successfully done only as several precautions are taken, namely: (a) very high purity starting materials should be used; (b) the solution of monomers and buffer should be degassed to remove oxygen; (c) a free radical initiator and a catalyst must be quickly mixed into the degassed solution; (d) the solution should be quickly poured between two glass plates or down a glass tube, the lower end of which in either case is sealed to prevent leakage; and (e) the gelation should proceed with (i) oxygen largely excluded and (ii) adequate means for heat dissipation being present so that excess heat does not cause gel nonuniformities.

The cell employed for the preparation of the gel generally has a length of approximately 6 to 60 cm. Accordingly, the introduction of the gel-forming solution into such a long cell requires careful operation to prevent the solution from gelling before it is completely poured (which would prevent the preparation of a uniform polyacrylamide gel medium of the desired length). Thus, the preparation of a polyacrylamide gel medium for electrophoresis having the desired dimensions and consistency requires a great deal of skill and care, as well as keeping the solution free from oxygen.

Precautions are also required in handling the monomers since both acrylamide and bis have been identified as known neurotoxins and suspected carcinogens.

There are several alternatives to the above-described procedure whereby the user makes electrophoresis gels by free radical polymerization and crosslinking in situ. These include (a) the use of preformed gels in cassettes and (b) the use of preformed gels on flexible supports. With either of these alternatives, however, some operating freedom or flexibility with regard to gel size, polymer content in the gel and buffer content is lost. Also—especially with precast gels in cassettes made by free radical polymerization and crosslinking—there generally remain, after completion of the gel formation reaction, some unreacted monomers, initiator by-products and catalyst. The presence of such species poses some toxicological hazards to the user and may interfere with the electrophoretic separation to be performed. Also, such precast gels have been found to have limited shelf lives.

U.S. Pat. No. 4,582,868, among others, describes the crosslinking of acrylamide-rich copolymers to form electrophoresis gel media by a non-free radical induced mechanism that does not require exclusion of oxygen. Typically, copolymers of acrylamide and a monomer that affords sites for subsequent non-free radical initiated crosslinking by treatment with a crosslinking agent, for example, an acrylamide derivative such as N-[3-(2-chloroethylsulfonyl)propionamidomethyl]acrylamide,

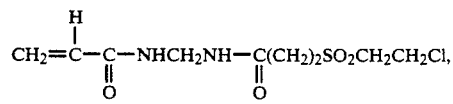

an acrylate derivative such as 2-[3-(2-chloroethylsulfonyl)propionyloxy]ethyl acrylate,

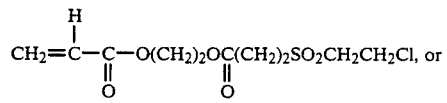

an active ester such as N-[2-(ethoxycarbonylmethoxycarbonyl)ethyl]acrylamide:

are prepared, in accordance with U.S. Pat. No. 4,582,868, by a free radical initiated polymerization in the absence of oxygen. Thereafter, in a separate procedure, which can safely be performed in the presence of oxygen, the chloroethylsulfonyl or other pendent reactive group-containing polymers are crosslinked by reaction at a suitable pH with a bis-nucleophile crosslinking agent such as a diamine or a dithiol. In this regard, it is noted that electrophoresis often is performed at pH values that facilitate dehydrohalogenation of the chloroethylsulfonyl groups. If the vinylsulfonyl groups so formed are not all reacted with the intended crosslinking agent, they could react with amino groups on dissolved proteins during electrophoresis. Such reaction would artifactually retard the electrophoretic migration of proteins and consequently give misleading electrophoresis results vis-a-vis the results obtained with electrophoresis gels formed by the free radical polymerization of acrylamide and bis alone. Therefore, enough crosslinking agent should be used to assure complete reaction of these groups.

Despite the availability of the above-described alternatives, electrophoresis media are still generally prepared by the polymerization of vinyl monomers at the time of use. This necessarily involves exposure of the operator to monomers prior to use and to residual monomers during use. Such monomers are suspected carcinogens, and at least some are known to be neurotoxins.

Although bis is the most widely used crosslinker for acrylamide-based electrophoresis gels, bis-crosslinked gels generally cannot be resolubilized. The ability to solubilize the gel after performing electrophoresis is advantageous in that it enables one to recover a resolved species from the gel. The use of an alternative, cleavable crosslinker such as diallyltartardiamide (DATD)

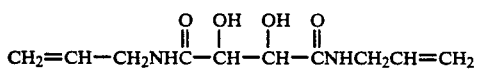

permits the researcher to achieve such recovery. After electrophoresis, each portion of the gel to be solubilized is excised and treated in a dilute solution of periodic acid. The —CHOH—CHOH— linkage in the middle of the crosslink is cleaved in the periodic acid solution and a solution of the thus solubilized polymer is produced. From this solution one can easily recover the resolved species for further experiments. Obviously, it would be advantageous to provide researchers with the option of gel solubilization after electrophoresis.

Also, if electrophoresis is to be performed soon after gelation, the chemical reaction (i.e., crosslinking) responsible for gelation must be compatible with the buffers present for electrophoresis. Gel electrophoresis is often performed at pH values ranging from 5 to 9.

A particularly popular system for the determination of molecular weights of proteins by electrophoresis was described by Laemmli [Nature, 227:680, (1970)]. In this system, two gels are used, one directly above the other, with a multi-phasic buffer system. The upper (or stacking) gel is at pH 6.8, which is achieved with tris(hydroxymethyl)aminomethane to which HCl has been added to lower the pH. The stacking gel has a low polymer concentration (generally from 4 to 6% w/v). Its purposes are (a) to provide a medium onto which samples can be loaded in discrete lanes and (b) to concentrate all species in a particular sample at the interface between the stacking gel and the lower (or resolving) gel. In meeting objective (b), the solutes, which are generally sodium dodecylsulfate (SDS)-denatured proteins, are "stacked" together (or very nearly so) i.e., are concentrated at the interface of the two gels, just before entering the resolving gel. For the stacking to occur effectively, the proteins, rather than the buffer, should carry most of the current and there should be no molecular size separation.

Molecular size separation occurs in the resolving gel, where the buffer carries most of the current and the solutes migrate at a velocity determined by the voltage gradient and the retardation due to the pore size distribution of the crosslinked polymer gel. The pH in the resolving gel is typically 8.8 and the polymer concentration is usually at least 10% (w/v).

In summary, the popular Laemmli procedure requires two gels, the lower of which (resolving gel) is larger (thereby providing a longer path for solutes to traverse) and contains a higher concentration of the gelled polymer, and therefore a smaller average pore size than that of the upper, or stacking gel. The conditions recommended by Laemmli are:

|  | Stacking Gel | Resolving Gel |
|---|---|---|
| pH | 6.8 | 8.8 |
| buffer | 0.125 M Tris.HCl | 0.375 M Tris.HCl |
| gel conc., % (w/v) | 4–6 | >10 |

Despite the various advances in electrophoresis technology, there is still a need for further improvements so that one not only can coat the solutions to be gelled in the presence of oxygen but also can easily and safely (a) pour such solutions into tubes or between plates, (b) form gels quickly and (c) solubilize gels or portions thereof for sample recovery after electrophoresis.

SUMMARY OF THE INVENTION

In one aspect, the present invention provides new compositions of matter which are monomers conforming to the structure:

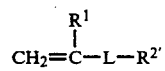

wherein $R^1$ is hydrogen or methyl, $R^{2'}$ is a haloacetamido group, preferably a chloroacetamido group, and L is an alkylene, an arylene, or combination of alkylene and arylene groups, all as more particularly defined hereafter, preferably L is an —$(R^3)_k$—(COXR$^4$—$)_m$—(NHCO)$_n$— group where $R^3$ is arylene, preferably phenylene; or arylene —$R^4$— wherein $R^4$ is alkylene of 1 to 6 carbon atoms, preferably phenylenemethylene; X is —O— or —NH—; and k, m, and n are each 0 or 1, provided that k is 0 when m is 1, and m is 0 when k is 1.

In another aspect, this invention relates to new polymeric compositions of matter which are homo- or copolymers comprising recurring units derived from at least one monomer conforming to Structure I. Preferred new polymers are those conforming to Structure II.

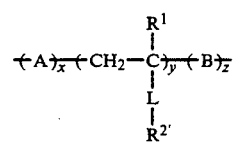

wherein L is as defined above for Structure I, —A— represents recurring units derived from one or more polymerized acrylamide monomers such as acrylamide, N-isopropylacrylamide, 2-acrylamido-2-hydroxymethyl-1,3-propanediol, etc., preferably acrylamide. $R^1$ is hydrogen or methyl; $R^{2'}$ is a haloacetamido group; —B— represents recurring units derived from any other polymerized vinyl monomers including divinyl and diacrylic monomers such as divinylbenzene, ethylene diacrylate, ethylene dimethyacrylate, N,N'-methylenebisacrylamide, etc; and x, y, and z represent weight percents of the recurring units, x being about 50–90, preferably 80–95 weight percent; y being about 1–50, preferably 5–20 weight percent, and z being about 0–45 weight percent.

In yet another aspect, this invention relates to electrophoresis media comprising crosslinked polymers which, before crosslinking, conform to the structure:

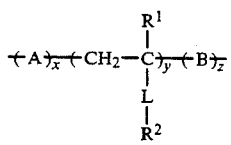
III wherein —A— represents recurring units derived from one or more polymerized acrylamide monomers such as acrylamide, N-isopropylacrylamide, 2-acrylamido-2-hydroxymethyl-1,3-propanediol, etc, preferably acrylamide; $R^1$ is hydrogen or methyl; $R^2$ is a halomethyl, haloacetyl, or haloacetamido group, preferably a haloacetamido group; L is a

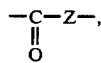

an alkylene, an arylene group a divalent heteroatom, or combination of

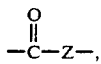

alkylene, divalent heteroatom, and/or arylene all as defined hereinafter; Z is a divalent heterocyclic group having about 5 to 7 nuclear carbon and heteroatoms such as a 1,4-piperazinylene; —B— represents recurring units derived from any other polymerized vinyl monomers including divinyl and diacrylic monomers such as divinylbenzene, ethylene diacrylate, ethylene dimethacrylate, N,N'-methylenebisacrylamide, etc; and x, y, and z represent weight percents of the recurring units, x being about 50–90, preferably 80–95 weight percent, y being about 1–50, preferably 5–20 weight percent, and z being about 0–45 weight percent.

L can be any linking group which is a substituted or unsubstituted alkylene generally having 1 to 20 carbon and heteroatoms in the backbone. This definition of alkylene is meant to include alkylene groups interrupted or terminated with oxy, thio, —$NR^3$—, wherein $R^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl, or xylyl), —Z— (as defined above), ester (—COO—), amide (—CONH—), urylene (—NHCONH—), urethane (—NHCOO—), sulfonyl (—$SO_2$—), carbonate, sulfonamide, azo, phosphone or other similar groups. Representative alkylene groups include methylene, ethylene, isobutylene, hexamethylene, carbonyloxyethoxycarbonyl, methylenebis(iminocarbonyl), carbonyloxydodecylenecarbonyloxyethylene, carbonyliminomethyleneiminocarbonyliminoethylene, carbonyliminomethyleneiminocarbonylethylene, carbonyliminotrimethyleneiminocarbonyl, carbonyloxyethyleneiminocarbonyl, and other groups described or suggested by U.S. Pat. Nos. 4,161,407 and 4,548,870.

L can also be a divalent heteroatom (or heteroatom-containing group) such as oxy, thio, —$NR^3$— where $R^3$ is as defined above, ester (—COO—), amide (—CONH—), urylene (—NHCONH—), urethane (—NHCOO—), sulfonyl (—$SO_2$—), carbonate, and sulfonamide.

L can also be substituted or unsubstituted arylene generally having 6 to 12 nuclear carbon atoms. Representative arylene groups include phenylene, tolylene, naphthylene, and others noted in the patents mentioned above. Also included in this definition of L are divalent groups which are combinations of two or more of any of the divalent heteroatom,

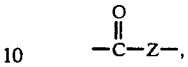

alkylene, and arylene groups defined above (e.g., phenylene, arylenealkylene, alkylenearylenealkylene, phenyleneiminocarbonyl, and others readily determined by one of ordinary skill in the art). Preferably, L is substituted or unsubstituted alkylene interrupted and/or terminated with heteroatom-containing groups as defined or a combination of phenylene and alkylene groups.

In yet another embodiment, the copolymer of the present invention, whether in the form of a resolving gel, stacking gel or both, is provided in a kit for preparing an electrophoresis gel, this kit comprising the copolymer and, in a separate container from the copolymer, a suitable crosslinking agent for crosslinking the copolymer by a reaction that does not involve a free-radical initiated vinyl addition mechanism. Optionally, the kit may also contain a selected buffer and other suitable ingredients for incorporation into the electrophoresis medium.

Acrylamide monomers are more stable to hydrolysis than acrylic esters, and they polymerize more readily with other acrylamide monomers than do other vinyl or acrylic monomers, e.g., esters. Therefore, acrylamide monomers and monomers having amide linkages, and particularly monomers wherein $R^2$ is a haloacetamido group, are preferred.

Representative new monomers of this invention are:

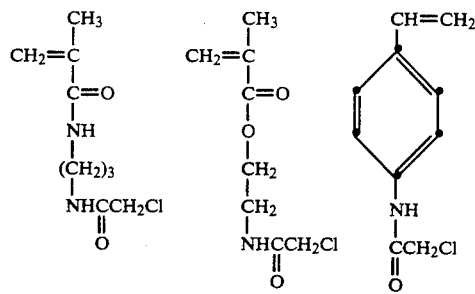

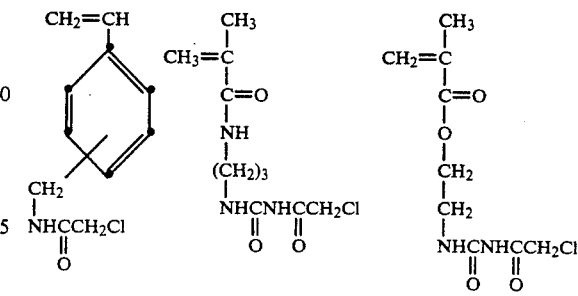

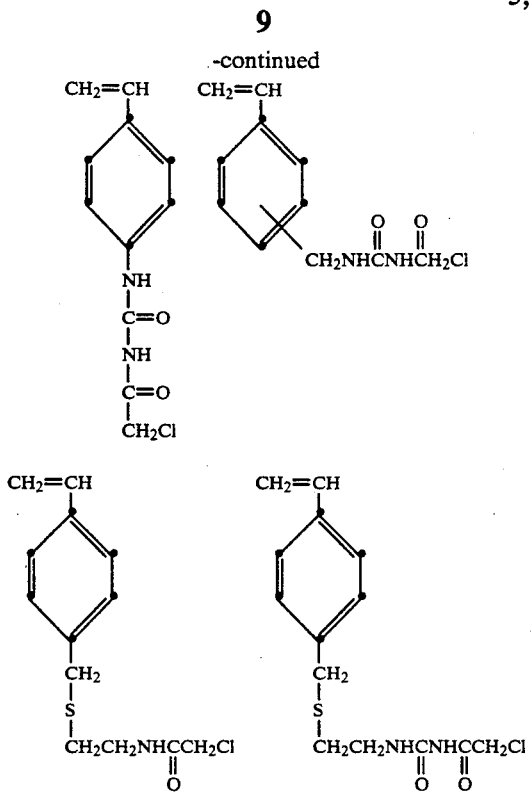

-continued

The foregoing polymers can be crosslinked with agents having two or more amino, mercapto, or phenolic hydroxy groups such as ethylenediamine, 1,3-propanediamine, 1,3-propane-dithiol, dithiothreitol, dithioerythritol, 1,5-pentanediamine, hexamethylenediamine, diethylenetriamine, triethylenetetramine, propylenediamine, di(aminomethyl)ether, 1,8-diamino-4-(aminomethyl)octane, xylylenediamine, hydroquinone, bisphenol A, bisphenol sulfone, thioethanolamine, p-aminothiophenol, and butylenediamine.

We have found that the weight average molecular weight $\overline{M}_w$ and the number average molecular weight $\overline{M}_n$ are important parameters that should be properly selected in order for a preformed polymer that is subsequently crosslinked with a chemical crosslinking agent that does not involve a free-radical vinyl addition mechanism, first to produce a gellable polymer solution for forming a resolving electrophoresis gel that (1) is easily poured into a slot (mold, tube, or between glass plates) no greater than 0.15 cm thick, (2) has a short gel time (i.e., about 4 to 10 minutes; by "gel time" is meant the time from addition of the crosslinking agent until the solution cannot be poured easily), but (3) remains pourable into said slot for a sufficient time to fill an electrophoresis mold of 14×14×0.15 cm (which takes about 4 to 6 minutes); and second, within about 10 minutes to 2 hours after addition of the crosslinking agent, to produce a firm gel having (1) sufficient crosslink density to afford good molecular sieving during electrophoresis, (2) good resolution during electrophoresis, (2) good resolution during electrophoresis, and (3) sufficient physical integrity to permit manual removal of the hardened gel from the mold shortly after electrophoresis as well as its handling without causing detrimental flow, compression, fracture, stretch, tear, or disintegration of the gel.

The requirements of $\overline{M}_w$ and $\overline{M}_n$ in said preformed polymer component of the electrophoresis media are:

1) $M_w$ is small enough that the addition of 1.25 to 1.5 times the stoichiometric amount of the selected cross-linking agent will not raise the viscosity of the mixture so much that the media cannot be poured into a 0.15×14×14 cm mold within about 4 to 10, preferably about 6 to 8 minutes after addition of the crosslinking agent, 2) $\overline{M}_n$ is large enough to provide a crosslink density sufficient to form a gel after about 10 minutes after addition of 1.25 to 1.5 times the stoichiometric amount of the selected crosslinking agent, said gel ultimately having sufficient integrity within about 2 hours after pouring to be removed from the mold and handled gently without tearing or falling apart, and 3) the number of equivalents of cross-linking sites per gram of polymer is in the range of $0.45(10^{-4})$ to $14(10^{-4})$, preferably at least $2/\overline{M}_n$; more preferably from about $2.25(10^{-4})$ to $10(10^{-4})$, most preferably about $4(10^{-4})$ to $7(10^{-4})$.

More particularly, for a copolymer of the present invention used for preparing a resolving gel for electrophoresis, the water soluble copolymer should have a number average molecular weight, $\overline{M}_n$, of at least about 7,000, preferably from about 7,000 to about 30,000, and a weight average molecular weight, $\overline{M}_w$, of less than about 100,000, preferably from about 25,000 to about 100,000.

When a copolymer of this invention is used to prepare a stacking gel composition, these molecular weights are each significantly higher than those of the resolving gel when polymers of exactly the same chemical composition are used. The $\overline{M}_n$ is preferably greater than about 50,000 and $\overline{M}_w$ is greater than about 100,000, preferably greater than about 150,000. The gel time is somewhat longer than that of the resolving gel because stacking gels are formed at a lower concentration (4–6% vs about 12%) and a lower pH (6.0–8.0) than resolving gels.

The following examples illustrate the practice of this invention.

EXAMPLE 1

Preparation of N-(3-Chloroacetamidopropyl)methacrylamide

In a 3-liter 4-neck flask fitted with condenser, stirrer, and 2-dropping funnels were placed N-(3-aminopropyl)methacrylamide hydrochloride 157 g 0.88 moles) in methanol (1.2 L) and 2,6-ditert-butyl-p-cresol (1.0 g). In one funnel was placed chloroacetyl chloride (100 g, 0.89 mole), and in funnel two was placed triethylamine (178 g, 1.76 mole). The solution was cooled to 0°–5° C. (ice-methanol), and triethylamine was added in a slow stream over 30 minutes, and the chloroacetyl chloride was added over 1 hour. After the addition, the temperature was maintained at 0° C. for 2 hours, the ice bath was removed, and stirring was continued at room temperature overnight. The solvent was removed, and to the residue was added hot ethyl acetate (500 mL). The mixture was filtered to remove triethylamine hydrochloride, then the solid was washed with hot ethyl acetate (500 mL), filtered again, the filtrate combined, and the solvent was removed on a rotory evaporator. The residue was crystallized from ethyl acetate (400 mL) by heating to dissolve, filtering to remove any solid present, and cooling to 0° C. to crystallize. The crude monomer was purified by chromatography on a silica gel packed column. The product was eluted from the column using a 1:1 mixture of ethyl acetate and dichloromethane (4 L). The collected solvent was evaporated, and the residue crystallized from ethyl acetate (300 mL) with 2,6-di-tert-butyl-p-cresol (500 mg) to give a white crystalline compound, mp 85°–90° C., 83 g (43% yield).

Anal. Calc'd for $C_9H_{15}ClN_2O_2$: C, 49.4; H, 6.9; N, 12.8; cl, 16.2. Found: C, 49.0; H, 7.6; N, 13.2; Cl, 17.3.

EXAMPLE 2

Preparation of Poly[acrylamide-co-N-(3-chloroacetamidopropyl)methacrylamide] (weight ratio 95/5)

To a mixture of acrylamide (electrophoresis grade) (34.2 g, 0.48 mole) and N-(3-chloroacetamidopropyl)methacrylamide (1.8 g, 0.008 mole) in tert-butanol (400 mL) and isopropanol (40 mL), maintained under a nitrogen atmosphere, was added 2,2'-azobis(2-methylpropionitrile) (1.0 g). The solution was heated to 70° C. in a thermostated bath for 6 hours (the polymer precipitates from solution after 10 minutes). The polymer was then filtered, washed with methanol (2L), acetone (2 L), sucked dry and placed in a vacuum over at 35° C. overnight to give a white powder; 36 g 100% yield. The polymer had an inherent viscosity of 0.42 dL/g in a 1.0 M sodium chloride solution measured at a concentration of 0.25 g/dL. Anal. Calc'd for $C_{3102}H_{5170}Cl_{17}N_{1017}O_{1017}$: C, 50.35, H, 7.04; N, 19.53; Cl, 0.76. Found: C, 48.3; H, 7.12; N, 18.18; Cl, 0.85.

Other polymers of the same family were prepared by varying the weight proportions of acrylamide and 3-chloroacetamidopropyl methacrylamide.

EXAMPLE 3

Alternate Preparation of Poly[acrylamide-co-N-(3-chloroacetamidopropyl)methacrylamide] (weight ratio 95/5)

This preparation employs a water/isopropyl alcohol solvent system instead of a t-butanol/isopropyl alcohol system.

A mixture of 68.4 g of acrylamide, 3.6 g of N-(3-chloroacetamidopropyl)methacrylamide, 600 mL of Milli Q water, 200 mL of isopropyl alcohol, and 4 g of 2,2'-azobis(2-methylpropionitrile) was placed in a 1000 L flask, purged with nitrogen gas for 10 minutes, and placed in a 63° C. constant temperature bath while stirring mechanically. After about 7 hrs. and 25 minutes, the flask was removed from the bath and allowed to cool overnight. The polymer product was precipitated by pouring into 4 L of acetone with stirring. The solvent was removed by filtration, the solid washed with 4 L of methanol, collected, washed again with 4 L of acetone, collected again on a filter, and dried overnight under vacuum.

EXAMPLE 4

Description of Use of Copolymers for SDS Electrophoresis

1. Stock Solutions
a. A 21.8% stock solution of the 95:5 poly[acrylamide-co-N-(3-chloro-acetamidopropyl)methacry lamide] was made by dissolving 21.8 g in high purity, deionized water (Milli Q) to a final volume of 100 mL.
b. a 22.5% stock solution of the 80:20 poly[acrylamide-co-N-(3-chloro-acetamidopropyl) methacrylamide] was made by dissolving 20 g in high purity, deionized water (Milli Q) to a final volume of 100 mL.
2. Preparation of 15% Resolving Gel To cast a 15% T gel, 6.88 mL of stock solution A representing [(1.5)(0.05)/218]0.000344 chemical equivalents of N-(3-chloroacetamido-propyl) methacrylamide was mixed with 0.05 mL of 20% sodium dodecyl sulfate (SDS), 1X equivalent of crosslinker (dithiothreitol), and the necessary volume of water to bring the total volume to 7.50 mL. After this solution is completely mixed, the solution is taken to a final volume of 10.0 mL with 2.5 mL of Tris-HCl, 1.5 M, pH 8.8. The buffer is added last since the crosslinking is pH dependent, and, if the buffer is added before the crosslinker, the gelation occurs too quickly. After adding the buffer, and mixing thoroughly, the mixture is poured between two glass plates, separated by a 0.075 cm slot, on a gel casting stand that had been previously set up. The mixture is poured within 1.5 minutes after adding the buffer, and the gel is completely poured within 5 minutes. After approximately 20 minutes, gelation begins and continues until the gel is firm.

If a stacking gel is to be used, step 3 is followed. If a stacking gel is not used, the teflon comb to form wells is inserted between the glass plates after the gel solution has been poured and kept there until the gel is firm.

3. Preparation of 5% Stacking Gel

After the a 15% T resolving gel was firm, a 5% stacking gel was layered over it. The 5% stacking gel was made by adding 2.2 mL of stock solution B representing [(0.5)(0.2)/218]0.000459 chemical equivalents of N-(3-chloroacetamidopropyl)methacrylamide. To this was added 0.05 mL of 20% sodium dodecyl sulfate, 0.83 mL Tris-HCl (pH 6.8, 1.5M), 1X equivalents of crosslinker (dithiothreitol), and high purity, deionized water (Milli Q) to a final volume of 10 mL. After thorough mixing, this was overlaid on the 15% resolving gel, and a teflon comb was inserted to form the stacking gel and loading wells for samples. The stacking gel became firm after approximately 6 hours.

4. Gel Electrophoresis Conditions

After the gel had been formed from part 2 (and part 3 if a stacking gel is used), the gel was used for a poly(acrylamide) gel electrophoresis experiment in the presence of sodium dodecyl sulfate and denatured proteins (SDS-PAGE).

The experimental conditions include:

a. Protein standards purchased from Bio-Rad Laboratories identified as high-molecular-weight and low-molecular-weight standards (c/n 161-0303 and 161-0304, respectively) that were dissolved in Tris-HCl, ph 6.5 (final concentration of 0.063M), sodium dodecyl sulfate, bromophenol blue tracking dye, and 2-mercaptoethanol (final concentration of 0.2%, 0.001%, and 5%, respectively) with glycerol added as a weighing agent to help concentrate the dissolved samples to the bottom of the sample well. Before the samples were loaded, the standards were heated at 95° C. for 5 minutes to denature the proteins.

b. The electrode running buffer was Tris-/glycine/SDS as described by U. K. Laemmli (Nature, 227:680, 1970), specifically 0.025M tris, pH 8.8, 0.19M glycine, and 0.1% SDS.

c. The teflon combs were removed from the gel (stacking gel if one is used) and an appropriate volume of standards from (4a) were added to the final protein concentration of high-molecular-weight standards was 7.5 μg (or 1.5 μg/protein standard and 9.0 μg of low-molecular-weight standard (or 1.5 μg/protein standard). The high-molecular-weight standard contained 5 proteins each having different molecular weight, and the low molecular-weight standard had 6 proteins each having a different molecular weight. The actual equipment used was the Hoefer model Se 250 vertical slab gel cell (San Francisco, Calif. 94107), and the procedure was described in the manual accompanying the Mini Protein II Dual Slab Gel (Electrophoresis) Cell sold by Bio-Rad Laboratories, Richmond, Calif. 94804.

d. The electrical parameters for the experiment were 100 volts, constant during the course of the experiment. The experiment was stopped when the bromophenol blue tracking dye was at the bottom of the gel, which was after approximately 2.3 hours under these conditions.

After the electrophoresis was completed, the gel was removed from the plates, and stained with 0.05% Coomassie Blue R250 dye solution containing acetic acid (10%), methanol (40%), and water (50%) for a minimum of 30 minutes. The dye preferentially adsorbs to the protein-rich areas, giving dark protein bands (after destaining with 10% acetic acid, 40% methanol, and 50% water) that leaves no doubt that the electrophoretic migration had taken place according to molecular size with good resolution. A graph of the migration distances (corrected for swelling due to destaining) plotted as abscissae and the logarithm molecular weights plotted as ordinates was nearly linear which is what one typically observes for SDS-PAGE. Thus, the gel medium provided results very similar to those obtained in SDS-PAGE gels made from acrylamide/bis polymerization.

EXAMPLE 5

Preparation of electrophoresis gel

An electrophoresis gel was made with poly[acrylamide-co-N-(3-chloroacetamidopropyl)methacrylamide] (weight ratio of acrylamide to comonomer: 90/10; mole ratio: 96.5/3.5) copolymers disclosed herein. This gel included a lower resolving gel made from poly[acrylamide-co-N-(3-chloroacetamidopropyl)methacrylamide] (weight ratio of acrylamide to comonomer: 90/10; mole ratio: 96.5/3.5) of $\overline{M}_n = 17.8$ ($10^3$) and $\overline{M}_w = 78.2$ ($10^3$) and a stacking gel from a poly[acrylamide-co-N-(3-chloroacetamidopropyl)methacrylamide] (weight ratio of acrylamide to comonomer: 90/10: mole ratio 96.5/3.5) of Example 2 [$\overline{M}_w \approx 500$ ($10^3$)].

The molecular weight averages of the acrylamide/N-(3-chloroacetamidopropyl)methacrylamide copolymers were estimated using an aqueous gel permeation chromatography system in which (a) the fractionation was accomplished with four TSK-GEL (type PW) columns of 6000, 5000, 3000 and 2000 Angstrom permeability limits (Altex Scientific, 1780 Fourth St., Berkeley, CA 94710), (b) the eluent was 0.05M Na$_2$SO$_4$ in 5% ethylene glycol-in-water (v/v), (c) the calibrating standards were Shodex STANDARD P-82 polysaccharides of 853, 380, 186, 100, 48.0, 23.7, 12.2 and 5.8 ($10^3$) (Showa Denko K. K., 280 Park Ave., 27th Floor West Building, New York, NY 10017) used at 0.1% (w/v) concentration, (d) the flow rate was 1.5 ml/min and (e) the detection of solute in the column effluent was done refractometrically.

Each copolymer was crosslinked with dithiothreitol used at 125% of the stoichiometric amount based on the number of crosslinking sites present. The pH of, and buffers used in, the gels and the electrode chambers are summarized in Table I.

TABLE I

| Location | Buffer pH | Composition |
|---|---|---|
| Cathode | 8.3 | 0.025 M Tris, 0.192 M glycine, 0.1% SDS |
| Stacking gel (4% polymer) | 7.8 | 0.125 M Tris.HCl |
| Resolving gel (12% polymer) | 9.4 | 0.375 M Tris.HCl |
| Anode | 8.3 | same as cathode except SDS was omitted and 0.1 M sodium acetate beneficially added (These variations from cathode conditions are optional.) |

Tris = Tris(hydroxymethyl)aminomethane
SDS = sodium dodecyl sulfate

In electrophoresis experiments conducted according to the Laemmli procedure with the buffer compositions given in Table I, the dithiothreitol crosslinked poly[acrylamide-co-N-(3-chloroacetamidopropyl)methacrylamide] (weight ratio of acrylamide to comonomer:90/10; mole ratio 96.5/3.5) copolymers of the present invention perform comparably to gels prepared from acrylamide and N,N'-methylenebisacrylamide. Specifically, the gels prepared from copolymers of this invention permit good electrophoresis separations, with SDS-complexed proteins with molecular weights from about 14.4 ($10^3$) to about 200 ($10^3$) appearing at the anode and cathode ends of the gel, respectively, after electrophoresis under conditions of voltage and time ordinarily used by those skilled in the art of electrophoresis for SDS-PAGE electrophoresis on acrylamide/bis gel media. Not only is the degree of separation comparable to that achieved with acrylamide/bis-based gels but the sharpness of the separated bands is also very good. These results can be achieved with gels in the so-called "mini" format (0.15 cm × 7 cm × 8 cm) (thickness × height × width) and in the popular larger format (0.15 cm × 16 cm × 14 cm).

The invention has been described in detail with particular reference to certain preferred embodiments thereof, but it will be understood that variations and modifications can be effected within the spirit and scope of the invention.

We claim:

1. An element for electrophoresis which comprises a crosslinked polymer which, before crosslinking, conforms to the structure

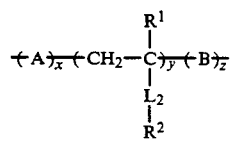

wherein —A— represents recurring units derived from one or more polymerized acrylamide monomers, R$^1$ is hydrogen or methyl, R$^2$ is a haloacetamido group, L is

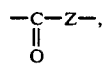

alkylene, arylene, a divalent heteroatom, or a combination of

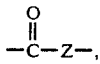

alkylene, divalent heteroatom, and/or arylene, Z is a divalent heterocyclic group having from 5 to 7 nuclear carbon and heteroatoms; —B— represents recurring units derived from any other polymerized vinyl monomer; and x, y, and z represent weight percents of the recurring units, x being about 50–90 weight percent, y being about 1–50 weight percent, and z being about 0–45 weight percent.

2. The element of claim 1 wherein L is an —$(R^3)_k$—$(COXR^4)_m$—$(NHCO)_n$— group where $R^3$ is arylene or arylene-$R^4$— wherein $R^4$ is alkylene of 1 to 6 carbon atoms, X is —O— or —NH—, and k, m, and n are each 0 or 1, provided that k is 0 when m is 1, and m is 0 when k is 1.

3. The element of claim 1 wherein $R^2$ comprises recurring units derived from N-(3-chloroacetamidopropyl)methacrylamide.

4. The element of claim 1 wherein an electrophoresis medium is used which is made by crosslinking in a reaction with a selected crosslinking agent that does not involve a free-radical vinyl addition mechanism, the copolymer being derived from a minor proportion of a comonomer that contains a site for the crosslinking reaction with the selected crosslinking agent, the preformed copolymer further having the following properties:

1) $M_w$ small enough that the addition of 1.25 to 1.5 times the stoichiometric amount of the selected crosslinking agent will not raise the viscosity of the mixture so much that the medium cannot be poured into a 0.15×14×14 cm mold within 4 to 10 minutes after addition of the crosslinking agent, and 2) $M_n$ large enough to provide a crosslink density sufficient to form a gel after about 10 minutes after addition of 1.25 to 1.5 times the stoichiometric amount of the selected crosslinking agent, the gel ultimately having sufficient integrity within 2 hours after pouring to be removed from the mold and handled gently without tearing or falling apart.

* * * * *

UNITED STATES PATENT AND TRADEMARK OFFICE
CERTIFICATE OF CORRECTION

PATENT NO. : 5,212,253
DATED : May 18, 1993
INVENTOR(S) : Ignazio S. Ponticello et al It is certified that error appears in the above-identified patent and that said Letters Patent is hereby corrected as shown below:

On the title page, Item [75] after "Rochester", ---; Hans W. Osterhoudt, Spencerport; all --- should be added and "both" should be deleted.

Column 14, lines 51-57 (Claim 1, lines 5-11), the structure should be

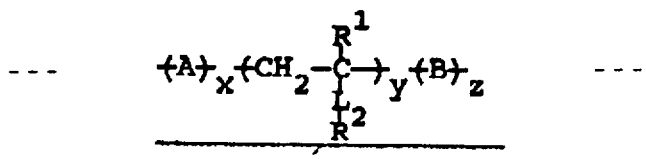

Signed and Sealed this

Twelfth Day of April, 1994

*Attest:*

BRUCE LEHMAN

*Commissioner of Patents and Trademarks*

*Attesting Officer*